United States Patent
Lefeuvre

(10) Patent No.: US 10,075,006 B2
(45) Date of Patent: Sep. 11, 2018

(54) AUTONOMOUS ELECTRONIC DEVICE WITH SUPPLY BY ELECTROSTATIC TRANSDUCTION PRODUCED BY A VARIABLE CAPACITOR

(71) Applicants: UNIVERSITE PARIS-SUD, Orsay (FR); CENTRE NATIONAL DE LA RECHERCHE SCIENTIFIQUE, Paris (FR)

(72) Inventor: Elie Lefeuvre, Montreuil (FR)

(73) Assignees: UNIVERSITE PARIS-SUD, Orsay (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 79 days.

(21) Appl. No.: 15/327,299

(22) PCT Filed: Jul. 17, 2015

(86) PCT No.: PCT/EP2015/066502
§ 371 (c)(1),
(2) Date: Jan. 18, 2017

(87) PCT Pub. No.: WO2016/009087
PCT Pub. Date: Jan. 21, 2016

(65) Prior Publication Data
US 2017/0179748 A1 Jun. 22, 2017

(30) Foreign Application Priority Data
Jul. 18, 2014 (FR) ...................................... 14 56987

(51) Int. Cl.
*A61N 1/00* (2006.01)
*H02J 7/00* (2006.01)
(Continued)

(52) U.S. Cl.
CPC .............. *H02J 7/0068* (2013.01); *A61B 5/07* (2013.01); *A61N 1/3787* (2013.01); *H02M 7/10* (2013.01);
(Continued)

(58) Field of Classification Search
CPC ..... A61N 1/3785; A61N 1/378; A61N 1/3787
(Continued)

(56) References Cited

U.S. PATENT DOCUMENTS

| | | | |
|---|---|---|---|
| 7,813,810 B2 | 10/2010 | Cernasov | |
| 2010/0298720 A1 | 11/2010 | Potkay | |
| 2014/0232240 A1 | 8/2014 | Hitchcock et al. | |

OTHER PUBLICATIONS

French Search Report for FR Application No. 1456987, dated May 27, 2015.
(Continued)

*Primary Examiner* — Amanda P Hulbert
*Assistant Examiner* — Philip C Edwards
(74) *Attorney, Agent, or Firm* — Greer, Burns & Crain, Ltd.

(57) ABSTRACT

An electronic device with a circuit for supplying electric power, with a variable capacitor, by alternating mechanical movement. The supply includes, in the form of passive components and without synchronizing structure:
generating branch including in series the variable capacitor and a biasing capacitor, connected in parallel to a rectifier circuit and a storage branch, between:
a base node, on the variable capacitor side;
an output node, on the biasing capacitor side;
unidirectional charge return branch:
to the generating branch, via a biasing node between the variable capacitor and the biasing capacitor;
from the rectifier, receiving a part of the electrical energy produced.

(Continued)

A circuit includes a voltage multiplier connected to the biasing node for applying a voltage that is multiplied relative to that existing between
the output node; and
the base node or one of the ends of the storage branch.

17 Claims, 11 Drawing Sheets

(51) Int. Cl.
| | |
|---|---|
| *H02N 1/08* | (2006.01) |
| *H02M 7/10* | (2006.01) |
| *A61B 5/07* | (2006.01) |
| *A61N 1/378* | (2006.01) |
| *H02J 7/34* | (2006.01) |

(52) U.S. Cl.
CPC ........ *H02N 1/08* (2013.01); *A61B 2560/0214* (2013.01); *H02J 7/345* (2013.01)

(58) Field of Classification Search
USPC ............................................................ 607/35
See application file for complete search history.

(56) References Cited

OTHER PUBLICATIONS

International Search Report for International Patent Application No. PCT/EP2015/066502, dated Nov. 6, 2015.

De Queiroz et al. "Analysis of the Doubler of Electricity Considering a Resistive Load" IEEE 56th International Midwest Symposium on Circuits and Systems (2013), p. 45-48.

Huang et al. "Low-Threshold Voltage Multipliers Based on Floating-Gate Charge-Pumps" IEEE Biomedical Circuits and Systems Conference (2008), p. 205-208.

Meninger et al. "Vibration-to-Electric Energy Conversion" IEEE Transactions on Very Large Scale Integration Systems (2001), 1(9), p. 64-76.

Torres et al. "Electrostatic Energy Harvester and Li-Ion Charger Circuit for Micro-Scale Applications" IEEE 49th International Midwest Symposium on Circuits and Systems (2006), p. 65-69.

Wardlaw et al. "Low-Power Circuits and Energy Harvesting for Structural Health Monitoring of Bridges" IEEE Sensor Journal (2013), 13(2), p. 709-722.

Yen et al. "A Variable-Capacitance Vibration-to-Electric Energy Harvester" IEEE Transactions on Circuits and Systems (2005), 53(2), p. 288-295.

Fig. 4
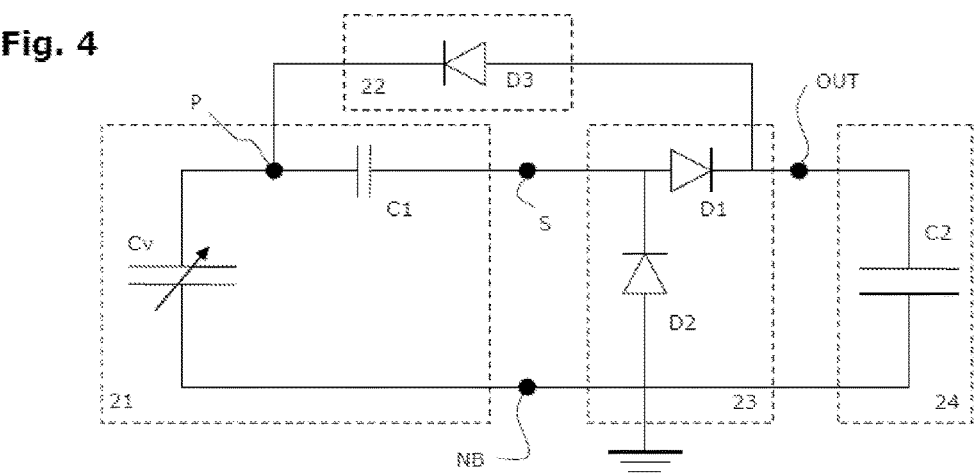
Fig. 5a
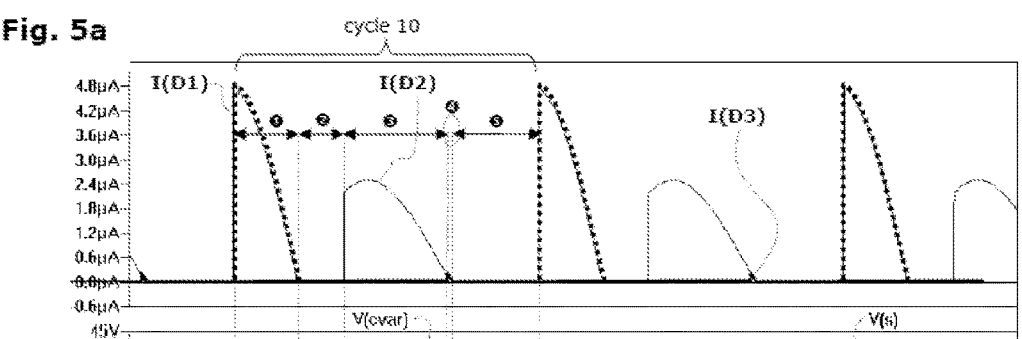
Fig. 5b
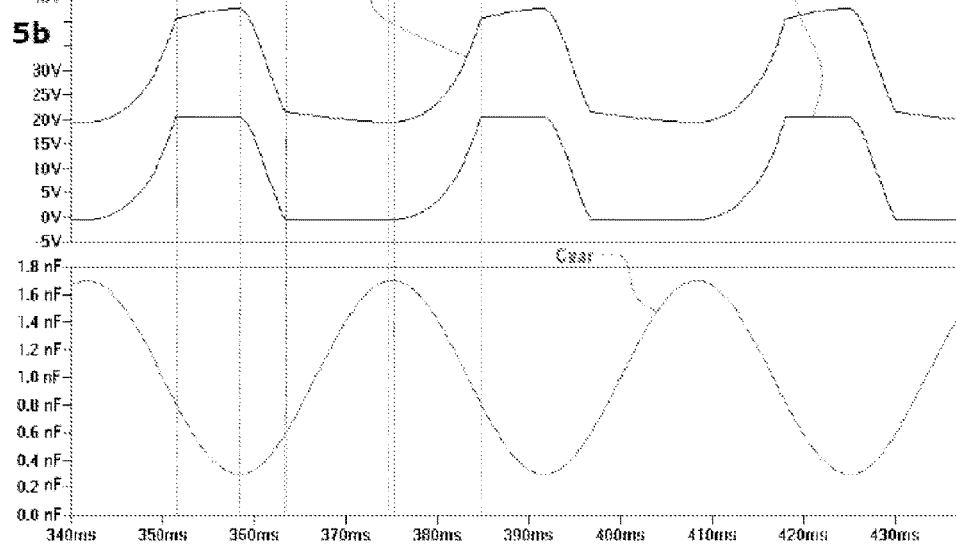
Fig. 5c phase 1 phase 2 phase 3 phase 4 phase 5

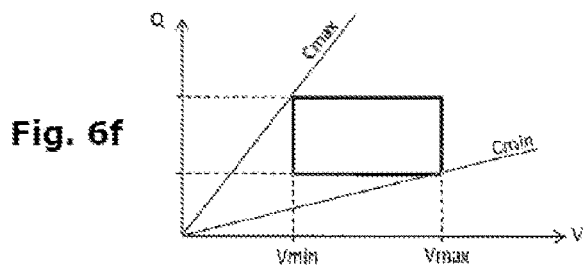
Fig. 6f
Fig. 7
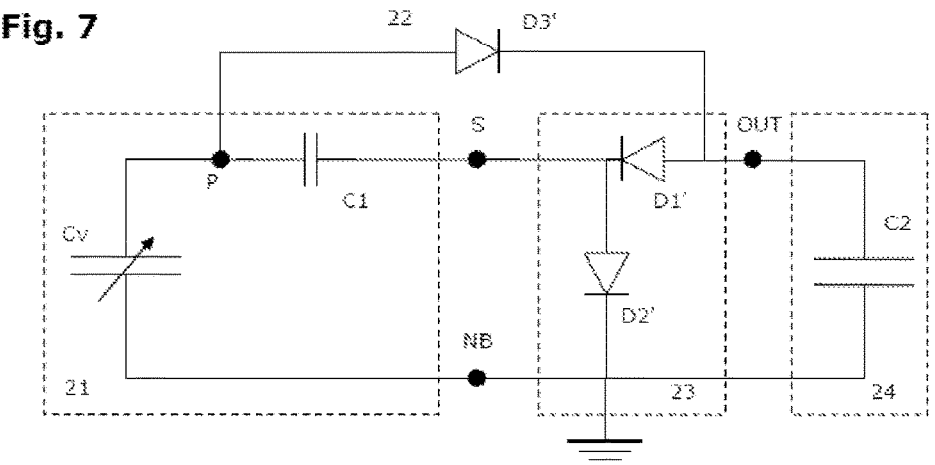
Fig. 8
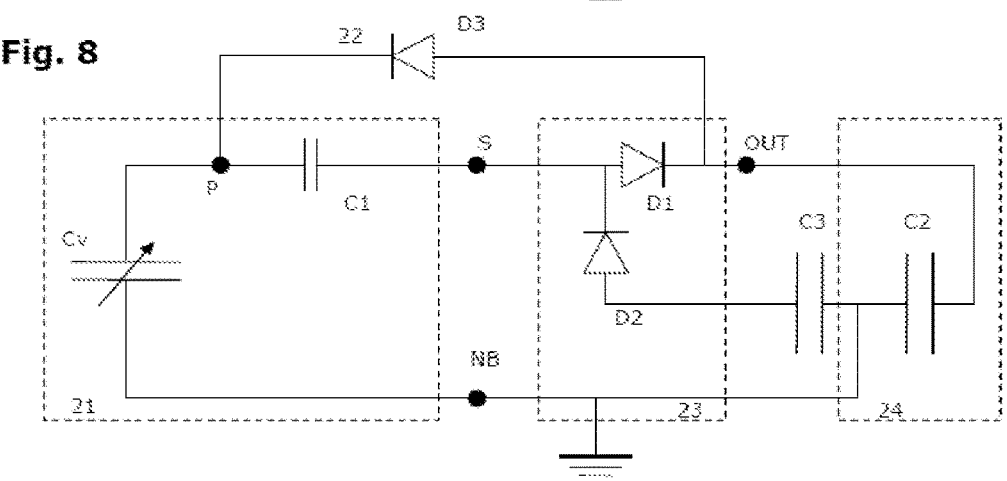
Fig. 9
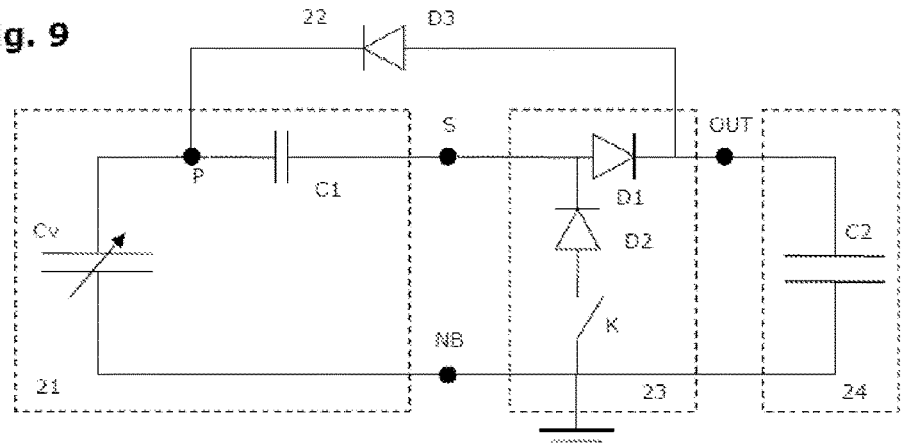

2-cell multiplier
$V_{cl} = 3 \cdot V_{out}$ type 1 multiplier type 2 multiplier type 3 multiplier type 4 multiplier type 1
parallel multiplier x1
$V_{c1} = V_{out}$ type 2
parallel multiplier x1
$V_{c1} = V_{out}$ type 1
parallel multiplier x2
$V_{c1} = 2.V_{out}$ type 2
parallel multiplier x 2
$V_{c1} = 2 \cdot V_{out}$ type 3
parallel multiplier x2
$V_{c1} = 2 \cdot V_{out}$ type 4
parallel multiplier x2
$V_{c1} = 2 \cdot V_{out}$ type 1
parallel multiplier x3
$V_{c1} = 3 \cdot V_{out}$ type 2
parallel multiplier x3
$V_{c1} = 3 \cdot V_{out}$ type 1
parallel multiplier x4
$V_{c1} = 4 \cdot V_{out}$ type 2
parallel multiplier x4
$V_{c1} = 4 \cdot V_{out}$ type 1
series multiplier x2
$V_{c1} = 2 \cdot V_{out}$ type 2
series multiplier x2
$V_{c1}=2.V_{out}$ type 3
series multiplier x2
$V_{c1}=2.V_{out}$ type 4
series multiplier x2
$V_{c1}=2.V_{out}$ type 1
series multiplier x3
$V_{c1}=3.V_{out}$ type 2
series multiplier x3
$V_{cl}=3.V_{out}$ type 3
with full bridge and
parallel multiplier x4
$V_{cl}=4.V_{out}$ type 4
with full bridge and
parallel multiplier x3
$V_{cl}=3.V_{out}$

AUTONOMOUS ELECTRONIC DEVICE WITH SUPPLY BY ELECTROSTATIC TRANSDUCTION PRODUCED BY A VARIABLE CAPACITOR

BRIEF SUMMARY

The invention relates to an electronic device of the type operating without an external power supply and comprising an electric power supply circuit comprising at least one variable capacitor, under the effect of an alternating mechanical movement, connected to a storage device by a rectifier circuit. This power supply circuit comprises, in the form of passive components and without synchronizing means:

- a generating branch comprising the variable capacitor and a biasing capacitor connected in series, said branch being mounted in parallel with the rectifier circuit and with a storage branch, between:
  - a node, called base node, at the end of the generating branch on the variable capacitor side,
  - a node, called output node, at the end of the generating branch on the biasing capacitor side;
- a unidirectional charge return branch:
  - to the generating branch at a biasing node located between the variable capacitor and the biasing capacitor;
  - from the rectifier, via at least one end receiving a part of the electrical energy produced.

According to the invention, the assembly formed by said generating branch, the rectifier circuit, the storage branch and the charge return branch constitutes an electric circuit that remains unchanged and permanent during at least one plurality of cycles of the variable capacitor.

This circuit thus produces, in each cycle, an additional charge of the biasing capacitor according to self-synchronizing operation, i.e. it does not require any means for synchronization with respect to the mechanical movements during said plurality of cycles.

Preferably, the power supply circuit comprises a voltage multiplier connected to the biasing node for applying a voltage that is multiplied relative to that existing between:
- the output node, and
- the base node or one of the ends of the storage branch.

The invention relates more particularly to an electronic device intended to be implanted in vivo in the human body or in the body of an animal without maintaining physical connection with the outside, and which comprises or forms an electronic device of this kind.

It further relates to an electric power supply circuit for forming the electric power supply circuit of such a device.

BACKGROUND

The field of the invention is that of electronic devices, or devices that comprise an electronic part, which must operate autonomously over an extended period of time without an external power supply, for much longer than would be permitted by the amount of power initially on board only.

Electronic devices of this kind may be for example devices with low consumption intended to be implanted in the human or animal body, for which it is impossible or complicated to provide an electrical connection for recharging. They may thus be for example measuring or detecting sensors with wireless communication, intended to be distributed or installed over wide areas, for example radio signal detectors, or environmental sensors in the natural environment, or any device for which considerable autonomy is required, for example devices intended to be worn as intelligent clothing, or on board in a system not intended to receive them, such as a surveillance or locating beacon.

It has been proposed to supply such a device, especially when a certain degree of miniaturization is sought, with electrical energy produced by a device forming a capacitor, the capacitance of which varies under the effect of mechanical energy received by the device itself. It may be for example a matter of recovering ambient mechanical energy, such as vibrations, variable mechanical deformations, variations in the pressure of a fluid, etc.

Such a manner of production converts mechanical energy to electrical energy by a transduction method called electrostatic transduction. From an electrical standpoint, the electrostatic transducer may be regarded as a variable capacitor. This manner of transduction passes through an electronic energy management circuit that can be miniaturized, but currently requires complex electronics for managing the charge and discharge cycles of the transducer.

Now, in the known devices, operation of such an energy management circuit requires several tens of volts and represents a sizable consumption, whereas the power levels generated by electrostatic devices are very low, typically in a range of power between a few nanowatts and a few hundreds of microwatts.

Among the first circuits proposed that operate at power levels of the order of the µW, a load-constrained conditioning circuit was proposed by Meninger et al. (2001) "Vibration-to-Electric Energy Conversion" in IEEE Transactions on Very Large Scale Integration (VLSI) Systems, Vol. 9, iss. 1, pp. 64-76, and a voltage-constrained conditioning circuit was proposed by Torres et al. (2006) 49th IEEE International Midwest Symposium on Circuits and Systems, MWSCAS '06, 6-9 Aug. 2006, pp. 65-69.

However, these two types of circuits are composed of switches synchronized with the mechanical movement of the transducer. The switches have to be controlled by an additional electronic circuit with high energy consumption compared to the power/energy generated. At present there is no viable implementation of this type of circuit for low powers, for example less than about a hundred microwatts.

As illustrated in FIG. 1, a circuit is proposed by Bernard C. Yen, "A Variable-Capacitance Vibration-to-Electric Energy Harvester", IEEE Transactions on Circuits and Systems, Vol. 53(2), pp. 288-295, 2005.

This circuit utilizes the variations in capacitance of the variable capacitor $C_{var}$ by using a charge pump composed of diodes and capacitors. The electrical energy generated by the capacitance is first stored in the capacitance $C_{store}$, and then sent periodically to $C_{res}$ by a return circuit via the inductance $L_{fly}$.

This circuit has drawbacks, however. In particular, the return circuit has an inductance that causes limitations in terms of circuit miniaturization.

Moreover, it also comprises a switch, the control of which must be adjusted as a function of the operating conditions of the electrostatic transducer, for example the state of charge of the capacitors $C_{res}$ and $C_{store}$, as well as the amplitude and frequency of the vibrations, so as to maximize the power generated. This control is provided by an intelligent circuit, which also consumes power.

A purpose of the invention is to supply an electronic device capable of converting ambient mechanical energy to electrical energy for its supply, in its entirety or as a supplement or prolongation of autonomy. The invention also seeks to optimize the efficiency of this conversion, the simplicity, reliability and the cost of its manufacture and operation.

SUMMARY

The invention proposes an electronic device of the type operating without an external power supply, preferably throughout its life or at least one cycle of operation. This operation may take place autonomously or with prolongation of autonomy, for example several weeks to several years possibly without material/physical connection with the outside or autonomously.

This device comprises an electric power supply circuit arranged to supply it, preferably entirely, but also as a supplement or prolongation of an on-board source. This electric power supply circuit is typically arranged to provide supply with a voltage that is stable, or does not exceed a maximum voltage suitable for an autonomous device, e.g. apparatus that is implanted or is transportable by an individual or on board within an energy-autonomous vehicle. It is typically low-voltage (less than 400V) or even extra-low voltage, for example less than 48V or even less than 12V, or 6V or 4V.

This power supply is preferably provided via a storage element, for example a capacitor or a supercapacitor or a rechargeable electrochemical battery. It may also be provided via an electrical energy consumer element, for example directly via the consumer load formed by operation of the device.

This electric power supply circuit comprises at least one component, called a variable capacitor, having an electrical capacitance that is variable under the effect of an alternating mechanical movement. Such a movement may be classified as oscillatory, in that it comprises movement between several extreme positions, even if said movement does not necessarily have a character of systematic regularity.

Such a movement typically takes place in several successive alternating phases, without continuity of direction (or of rotation) between these different phases. For example, this movement may be that produced by a drive mechanism or organ, for example beating of the heart or of another muscle.

It may comprise one or more components, each forming in itself a variable capacitor, i.e. capable in itself of increasing the load.

An important point of the invention is that it makes it possible to use, and proposes preferably doing so, such a variable capacitor formed by a variable capacitor, or several variable capacitors that operate in the same direction. That is, when there are several of them, they all vary in the same direction at each instant, and preferably are mechanically integral with one another. This characteristic allows considerable compactness and simplicity in the architecture of this or these variable capacitors, and in their integration within the electronic device thus supplied.

This variable capacitor:
is arranged to receive said mechanical movement from the environment of said electronic device, for example by inertia, displacement, or compression, and
is connected to said storage element by means of a rectifier circuit to increase the electrical energy that is stored there.

According to the invention, this electric power supply circuit comprises a generating branch formed by at least the variable capacitor and a biasing capacitor (preferably with fixed capacitance) mounted in series. This generating branch is mounted in parallel with the rectifier circuit and with a storage branch comprising the storage element. It is mounted between:
a node, called base node, which is located at the end of the generating branch on the variable capacitor side and is maintained at a reference potential (permanently or from one cycle to another),
a node, called output node, located at the end of the generating branch on the biasing capacitor side.

Thus, the potential between the variable capacitor and the biasing capacitor has an average value that varies when the charge increases in the storage element.

According to the invention, this electric power supply circuit further comprises a charge return branch of a type able to conduct a unidirectional electric current, for example in the form of one or more diodes. This charge return branch is thus conductive:
from the rectifier circuit, via at least one second end receiving a part of the electrical energy produced by said power supply circuit,
to the generating branch, via at least one first end connected to a node of the generating branch that is located between the variable capacitor and the biasing capacitor, i.e. to a common node or one connected to these two elements, and is called biasing node here.

Moreover, according to the invention, an electric power supply circuit of this kind comprises a circuit arranged to form a voltage multiplier circuit that is connected to the generating branch at a biasing node located between the variable capacitor and the biasing capacitor, for applying a voltage there that is multiplied relative to the voltage that exists between
on the one hand the output node of said generating branch, and
on the other hand to the base node or to one of the ends of the storage branch.

According to the invention, said generating branch, the rectifier circuit, the storage branch and the charge return branch form an assembly that constitutes an electric circuit, called a passive circuit, the behaviour of which is passive and which remains unchanged and permanent in its characteristics during at least one plurality of cycles of the variable capacitor, preferably a number of cycles greater by a factor of 100 or even 1000 or 10000. That is, for this period of time, this assembly has neither interruption, nor changes over time of the characteristics of these four elements. That is, these elements (including the multiplier circuit) form a circuit that is not modified from outside for a prolonged time, apart from the movement forced on the variable capacitor and the power supplied by the storage branch to the consumers that it supplies.

Thus, for a "passive" time covering several cycles, the components of this circuit are unchanged: they behave identically from one cycle to another, i.e. they react to the internal conditions of the circuit according to the same laws and with the same characteristics. Preferably, for this period of time, this specific circuit only communicates with the outside by the movement that it receives and the energy that it supplies, and is isolated from the rest of the outside world.

This passive circuit does not receive commands changing its structure during this passive period of time, as might be done for example by a command for change of state of a switch, or a blocking or conducting signal of a transistor. Throughout this time covering several cycles, the components of this circuit are unchanged: they behave identically from one cycle to another, i.e. they react to the internal conditions of the circuit according to the same laws and with the same characteristics. During such a period of time, this specific circuit only communicates with the outside by the movement that it receives and the energy that it supplies, and is isolated from the rest of the outside world. It is therefore an autonomous circuit, and stably so for a significant period of time.

For example, this passive circuit does not comprise components active at command input such as transistors; or if it comprises them, the latter are controlled with a period greater than said plurality of cycles, for example for a setting or an adjustment from time to time, for example daily or monthly in the case of a cardiac pacemaker at about 100 cycles per minute. In particular, the assembly formed by said generating branch, the rectifier circuit, the storage branch and the charge return branch does not comprise any magnetic component, i.e. any component of the inductance, coupled inductance or magnetic transformer type.

Thus, at each cycle, the power supply circuit carries out an additional charge of the biasing capacitor according to an operating mode that is self-synchronizing, i.e. it does not require any means for synchronization with respect to the mechanical movements during said plurality of cycles.

Operation is thus completely self-synchronizing, whatever the oscillation frequency and without requiring control by a switch or a transistor, at least for all of this "passive" period.

Optionally, some or all of the components mentioned here as being diodes are each replaced by a sub-circuit carrying out a "diode function", preferably based on components that are entirely passive and for example only with diodes, transistors and capacitors. Such a sub-circuit with "diode function" is for example a first diode to which a transistor is connected in parallel (for example via drain and source), which will short-circuit it when its command (grid) is activated by the output of a second diode that leads from the output of the first diode to an earthed capacitor. Such a sub-circuit makes it possible to carry out the function of a diode without having the voltage threshold of a simple diode. As the transistor is controlled directly by the conduction of the diode, without any external signal, such a sub-circuit behaves like a simple diode and still complies with the autonomous, self-synchronizing operation of the power supply circuit throughout the period called "passive" period.

Embodiments with Voltage Multiplier

According to a characteristic, the invention additionally proposes integrating a circuit of the voltage multiplier type within the electric power supply circuit of the device. This electric power supply circuit thus comprises a voltage multiplier circuit that is connected to the generating branch at a biasing node located between the variable capacitor and the biasing capacitor. This multiplier is connected and configured so that this biasing node has a voltage that is multiplied relative to the voltage that exists between:

on the one hand the output node of said generating branch, and on the other hand the base node or one of the ends of the storage branch.

Such a use of a voltage multiplier is particularly beneficial for improving the energy capacity converted in each cycle, especially when the variable capacitor has a small variation in its capacitance.

Voltage multipliers are known, for producing a large increase in voltage starting from a conventional source of alternating current without constraint on the amount of power, typically from a distribution network of 110V or 220V alternating current.

In contrast to these known uses, in the invention the multiplier overcomes the small variation of the variable transducer, which constitutes a major problem of the autonomous supplies based on an electromechanical transducer; especially in the types of apparatus envisaged here and more especially in equipment that is highly miniaturized and/or has a small mechanical travel.

According to a characteristic, the charge return branch comprises a diode oriented from the rectifier to the generating branch, or several diodes mounted in the same direction, and preferably in series.

More particularly, the electric power supply circuit, or at least one or more of the circuits among the generating branch, the storage branch, the charge return branch and the rectifier circuit, and the multiplier circuit, is produced (preferably in the form of a single integrated circuit) so that it only comprises passive components and non-driven semiconductors, and in particular only diodes and capacitors (in addition to the conductors that connect them together and optionally ohmic resistances).

The variable capacitor may use any type of technology, including electrically active polymers the capacitance characteristics of which vary with their deformation, such as those used for making artificial muscles.

However, the invention is particularly beneficial when used with one or more fluid-filled variable capacitors. They may for example be variable air capacitors operating by relative movement of the electrodes. They may also be variable capacitors operating by liquid displacement, for example producing a displacement of the dielectric material directly, or producing a relative displacement of the electrodes. In fact, these types of variable capacitors are particularly suitable for recovering mechanical energy of low power and/or with short travel, which is particularly beneficial for recovering energy of biological origin, for example for a device implantable inside the body such as a medical device for monitoring and/or stimulation.

According to a characteristic, the invention relates to a low-power autonomous device, for example less than one watt or even less than 500 mW or 100 mW.

According to another characteristic of the invention, an electronic device is proposed that is intended to be implanted in vivo in the human body or in the body of an animal without maintaining physical connection with the outside, characterized in that it comprises or forms an electronic device as described here.

According to another aspect of the invention, an electric power supply circuit is proposed for an electronic device as described here.

Other characteristics are envisaged and described in the rest of the present description. Various embodiments of the invention are envisaged, incorporating the various optional characteristics presented here in all of their possible combinations.

BRIEF DESCRIPTION OF THE DRAWINGS

Other advantages and characteristics of the invention will become apparent on examination of the detailed description of an embodiment which is in no way limitative, and the attached drawings, in which:

FIG. 4 is a diagram illustrating the power supply circuit of a device according to the invention, in a first embodiment or basic circuit;

FIG. 5a to FIG. 5c are timing diagrams illustrating the operating cycle of the power supply circuit in FIG. 4, with:
in FIG. 5a, the currents in the three diodes of the circuit, and
in FIG. 5b, the voltages at the terminals of the variable capacitor and at the terminals of the generating branch,
in FIG. 5c, the capacitance value of the variable capacitor;

FIG. 6f is a diagram illustrating the energy conversion cycle on the charge-voltage plane;

FIG. 7 is a diagram illustrating the power supply circuit of a device according to the invention, in a second embodiment forming an inverted version of the basic circuit in FIG. 4;

FIG. 8 is a diagram illustrating the power supply circuit of a device according to the invention, in a third embodiment based on the basic circuit and in which the storage capacitor is of a type with mid-point connected to the rectifier;

FIG. 9 is a diagram illustrating the power supply circuit of a device according to the invention, in a fourth embodiment comprising the basic circuit provided with a switch;

FIG. 16 and the subsequent figures are diagrams showing the power supply circuit of a device according to the invention of one of the embodiments with a multiplier, in versions with:

in FIG. 16, a voltage multiplier of type 1 of the parallel type, with a factor of 1.

in FIG. 32, a voltage multiplier of type 3 of the parallel type, with a factor of 4;
in FIG. 33, a voltage multiplier of type 4 of the series type, with a factor of 3.

DETAILED DESCRIPTION

Figure 2:
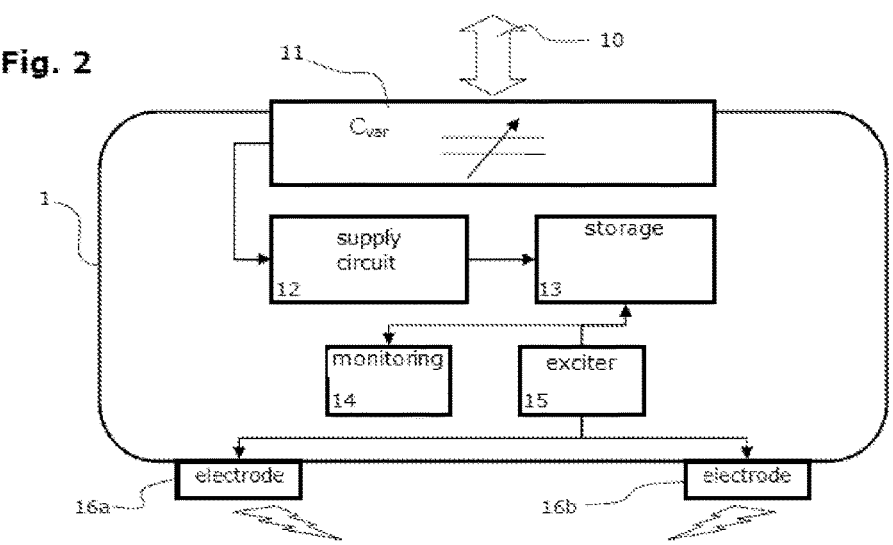
FIG. 2 is a schematic diagram of a device according to an embodiment example of the invention, applied to a cardiac pacemaker.

FIG. 2 is a schematic diagram of a device according to an embodiment example of the invention, applied to a cardiac pacemaker 1. A variable capacitor 11 is actuated by the heartbeats, and is connected to the power supply circuit 12, which increases the charge of a storage element 13, which for example may be a capacitor or a chemical accumulator. This energy is used by an exciting circuit 15 for supplying electrodes 16a and 16b, which stimulate the heart if necessary or according to a rhythm calculated by a control circuit 14, for example connected to detecting means (not shown here).

Figure 3:
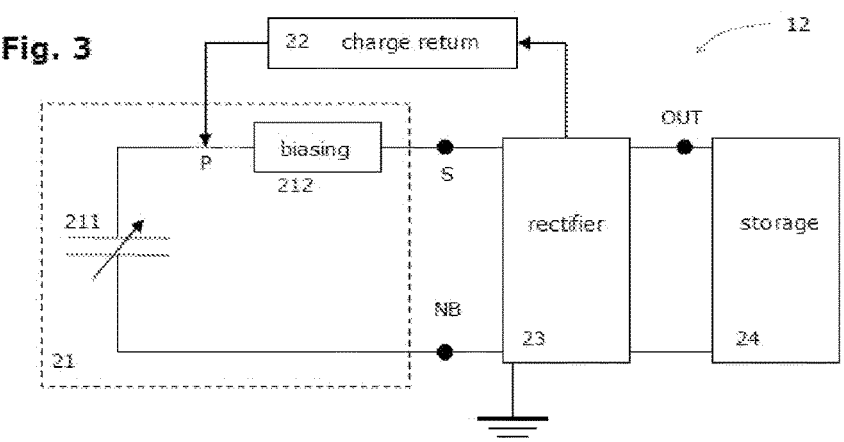
FIG. 3 is a schematic diagram of the electric power supply circuit of a device in an embodiment example according to the invention.

The invention proposes using a family of generation interface circuits, i.e. for power supply, the structure of which may be defined as follows, referring to FIG. 3.

The variable capacitor 211 is placed in series with a biasing component 212, for example a capacitor or a supercapacitor or an electric power accumulator.

The dipole thus formed constitutes a generating branch 21, which is connected to the input of a rectifier circuit 23, for example composed of diodes or other active electronic components carrying out the same function.

The output of the rectifier circuit 23 is connected to an electric power storage component 24, i.e. for example a capacitor, a supercapacitor, an electric power accumulator.

A charge return circuit 22 allows a voltage to be maintained at the terminals of the biasing component 212.

The biasing component 212 differs from the electric power storage component 24 in particular in that the energy stored in the former may be very low relative to that stored in the latter. Preferably, the energy stored in the biasing component 212 is at least ten times greater than that generated by the variable capacitor 211 during a conversion cycle.

Embodiment Called "Basic Circuit" Embodiment

FIG. 4 shows the power supply circuit of a device according to the invention, in a first embodiment, called "basic circuit" here.

In this embodiment, the power supply circuit comprises the following elements, and preferably only these:

a generating branch 21 comprising the variable capacitor Cv and one or more biasing capacitors C1, and preferably only these latter (and preferably only one). This generating branch is connected via its base node NB to a reference potential, which is earth here, by a node that is common to the rectifier 23 and to the storage branch 24;

a rectifier circuit 23 comprising the following components, and preferably only these:
  a diode D2 (preferably just one), or several diodes mounted in the same direction (preferably in series), from the base node NB to the end S of the generating branch that is located on the biasing capacitor C1 side,
  a diode D1 (preferably just one), or several diodes mounted in the same direction (preferably in series), from the end S of the generating branch 21 located on the biasing capacitor C1 side and to the OUT end of the storage branch 24 that is located on the side opposite the base node NB;

a storage branch 24 comprising a storage element, and preferably only the latter, said storage element comprising a capacitor C2 or a chemical storage element (and preferably only one of these); and a charge return branch 22 comprising a diode D3 (preferably just one), or several diodes mounted in the same direction (preferably in series), from the OUT end of the storage branch 24 located on the side opposite the base node NB and to the biasing node P located in the generating branch 21 between the variable capacitor Cv and the biasing capacitor C1.

Rectification is carried out by the diodes D1 and D2, forming a "half-bridge", while the charge of the biasing capacitor is provided by D2 and D3. It should be noted that D2 is used both in the rectification function and in the biasing function.

Preferably, the components are selected as follows:
Biasing capacitor: capacitor C1 comprised of $$C1 > 2 \cdot (C_{MAX} - C_{MIN}) \text{ or even } C1 > 5 \cdot (C_{MAX} - C_{MIN})$$

and for example capacitor C1 comprised between 2 and 10 times $(C_{MAX} - C_{MIN})$.
Storage capacitor (if it is not a battery): $C_{OUT} > 3 \cdot C1$
and for example capacitor C2 with a value between 10 times and 1 million times $(C_{MAX} - C_{MIN})$
Diodes: all diodes with very low leakage and very low parasitic capacitances.
The diodes are preferably selected with a leakage current less than five picoamperes, and for example with a breakdown voltage between 50 and 500V, for example of the order of 100V.

FIG. 5a to FIG. 5c are timing diagrams illustrating the operating cycle of the power supply circuit in FIG. 4, for components having the following values:

D1, D2, D3: diodes with low leakage current $I_{RMAX}=5$ pA (according to the reference of the components PAD5 or JPAD5)
Cvar: maximum value of $Cvar_{MAX}=1700$ pF, and minimum value $Cvar_{MIN}=300$ pF
C1: 10 nF
For operation at 30 Hz and $V_{OUT}=20$V, the average power generated is 11.5 µW.

FIG. 5a shows the typical waveforms of currents ID1, ID2 and ID3 respectively, which flow in the three diodes of circuits D1, D2 and D3 respectively.

FIG. 5b shows the voltages V(cvar) and V(s) respectively that are present at the terminals of the variable capacitor Cv and respectively at the terminals of the generating branch 21, i.e. between the base node NB and the output node S.

FIG. 5c shows the waveforms of the variation of the capacitance of the variable capacitor during the mechanical cycle 10.

FIG. 6a to FIG. 6e are diagrams of the circuit in FIG. 4, illustrating the currents passing through the circuit during the different phases 1 to 5 of the operating cycle that are indicated in FIG. 5.

Figure 6A:
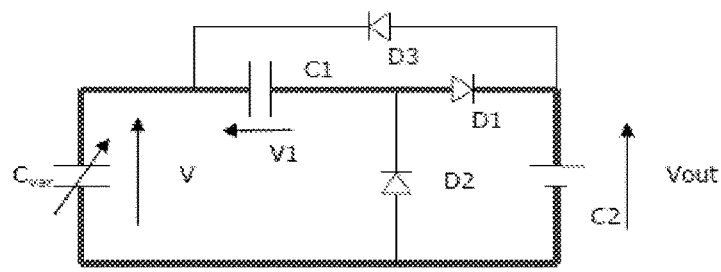
FIG. 6a to FIG. 6e are diagrams of the circuit in FIG. 4, illustrating the currents passing through the circuit during the operating cycle.

FIG. 6a shows phase 1: end of voltage rise V(cvar), and voltage plateau V(s). The variable capacitor decreases under the mechanical effect that is applied to it, which creates a current ID1 through diode D1 and thus charges the storage capacitor C2.

Figure 6B:
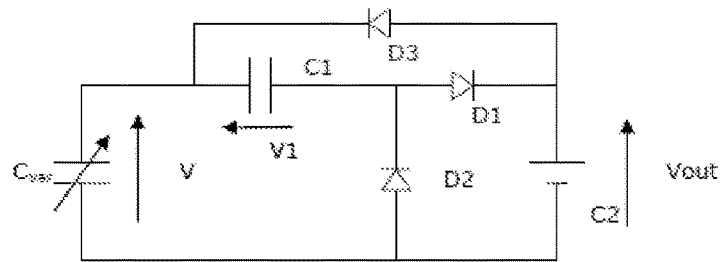

FIG. 6b shows phase 2: fall of voltage V(cvar) and of voltage V(s). The variable capacitor increases under the mechanical effect that is applied to it, but no current passes through the circuit. In fact, as the voltage V(s) is less than V(OUT) while being strictly positive, the diodes D1 and D2 are in the OFF state. Moreover, the voltage V(cvar) is greater than V(OUT), which keeps diode D3 in the OFF state.

Figure 6C:
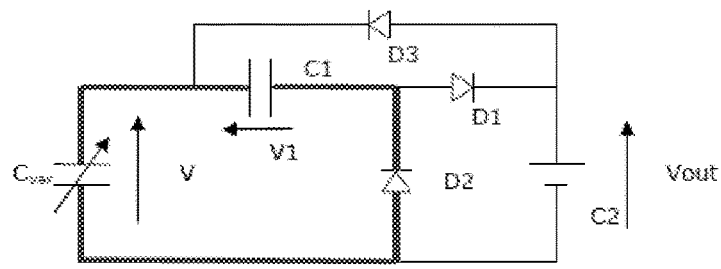

FIG. 6c shows phase 3: end of fall of voltage V(cvar), and voltage plateau V(s). The variable capacitor continues to increase under the mechanical effect that is applied to it, which creates a current ID2 through diode D2 and thus charges the biasing capacitor C1.

As can be seen, the repolarization charge of C1 is mainly created by the variable capacitor Cvar, with very little supply from the storage capacitor C2. Very efficient use of the variable capacitor is thus obtained, and low losses in the energy stored in C2.

Figure 6D:
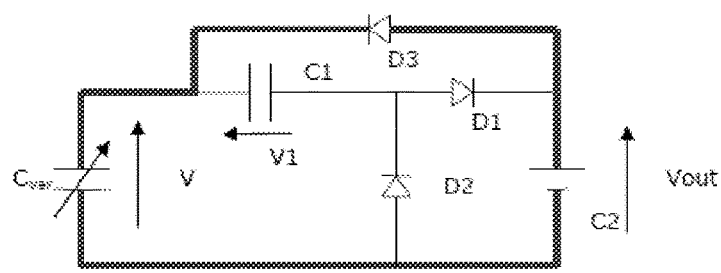

FIG. 6d shows phase 4: the variable capacitor reaches its maximum under the mechanical effect that is applied to it. A current ID3 passes very briefly through diode D3. In permanent operation, making D3 conductive thus allows additional charging of the biasing capacitor C1, for a very short time.

At the start of operation, this phase allows initial charging of the biasing capacitor C1, if necessary drawing from the storage capacitor C2, allowing the generating system to be started.

Figure 6E:
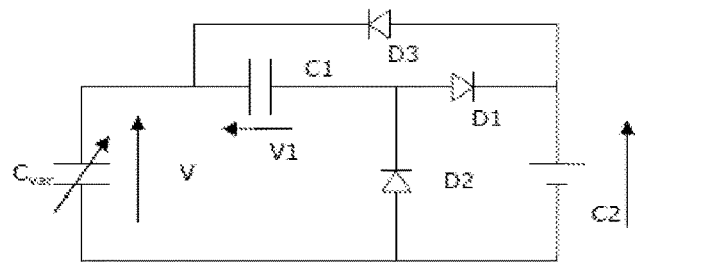

FIG. 6e shows phase 5: The variable capacitor decreases under the mechanical effect that is applied to it, but no current passes through the circuit. In fact, as the voltage V(s) is strictly positive while remaining less than V(OUT), diodes D1 and D2 are in the OFF state. Moreover, V(cvar) is greater than V(OUT), which keeps D3 in the OFF state. The voltages V(cvar) and the voltage V(s) increase and electrical energy is thus stored in the variable capacitor Cvar.

FIG. 6f shows the energy conversion cycle in the charge-voltage plane.

The charge-voltage cycle carried out at the level of the variable capacitor by this interface circuit is a rectangular cycle comprised between the straight-line slopes Cmin and Cmax, the minimum and maximum capacitances of the variable capacitor Cv.

In this figure, the area of the cycle is the energy converted per period of variation of the variable capacitor:

$$W = (V\text{max} - V\text{min}) \cdot (C\text{max} \cdot V\text{min} - C\text{min} \cdot V\text{max}) \tag{1}$$

Figure 1:
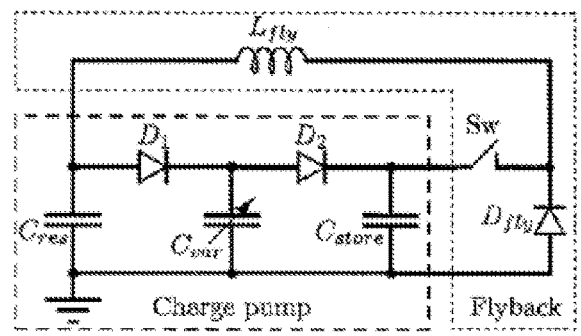
FIG. 1 is a diagram illustrating an electric power supply circuit based on a variable capacitor according to the prior art.

Vout denotes the output voltage of the interface, i.e. the voltage $Vc_{res}$ for the circuit in FIG. 1.

In the case of the circuit in FIG. 1, the voltage Vmax leads to an optimum energy conversion when it is satisfied (cf. thesis of Andrii Dudka (2014)):

$$V\text{max} = \frac{1}{2} Vout\left(\frac{C\text{max}}{C\text{min}} - 1\right) \tag{2}$$

The maximum energy converted is then:

$$W\text{max} = \frac{1}{4} Vout^2 \cdot C\text{min}\left(\frac{C\text{max}}{C\text{min}} - 1\right)^2 \tag{3}$$

In the invention, for the basic circuit illustrated in FIG. 4, the voltage Vmax is twice as high as Vout and the voltage Vmin is equal to Vout. The energy converted per cycle is therefore expressed as follows:

$$W\text{max} = Vout^2 \cdot C\text{min}\left(\frac{C\text{max}}{C\text{min}} - 2\right) \tag{4}$$

Figure 15:
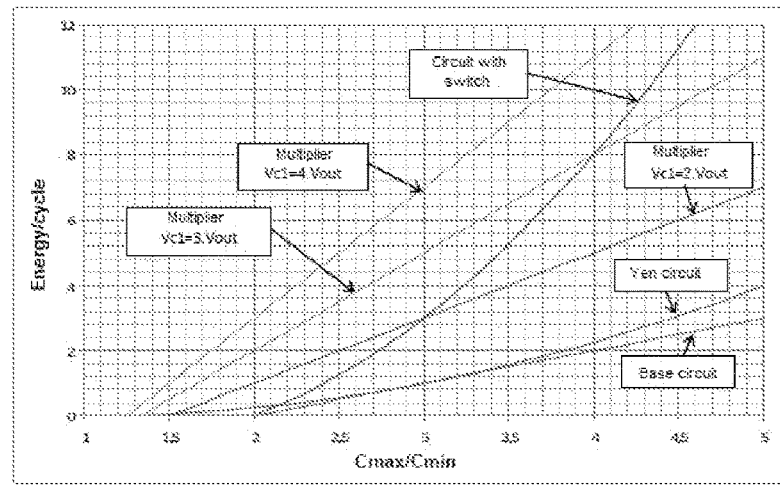
FIG. 15 is a graph representing the energy performance per cycle, obtained by simulation for different embodiments of the electric power supply circuit of a device according to the invention, compared with one another and with the circuit in FIG. 1.

Equations (3) and (4) make it possible to compare the maximum energy converted per cycle with the circuit in FIG. 1 and that converted with the circuit according to the invention in the basic circuit version in FIG. 4. As illustrated in FIG. 15, this basic circuit according to the invention may display performance close to the circuit in FIG. 1 (Yen), or slightly lower.

However, the circuit according to the invention offers several advantages relative to the circuit in FIG. 1, even in the basic version in FIG. 4, as it does not use a switch or an inductance. All the energy generated is supplied directly to the storage element, without an intermediate storage capacitor or a return circuit. This offers better opportunities for miniaturization, greater simplicity, and potentially better reliability. This simplicity may moreover also provide better performance under real conditions.

Variants of the Basic Circuit

"Inverted" Basic Circuit

FIG. 7 shows the power supply circuit of a device according to the invention, in a second embodiment forming an inverted version of the basic circuit in FIG. 4.

In this device, the power supply circuit comprises the following elements, and preferably only these:

a generating branch 21 comprising the variable capacitor Cv and one or more biasing capacitors C1, and preferably only the latter (and preferably only one), said generating branch being earthed via the base node NB;

a rectifier circuit 23 comprising the following components, and preferably only these:

a diode D2' (preferably only one), or several diodes mounted in the same direction (preferably in series), to the base node NB and from the output node S of the end of the generating branch 21 located on the biasing capacitor C1 side, a diode D1' (preferably only one), or several diodes mounted in the same direction (preferably in series), to the output node S of the end of the generating branch 21 located on the biasing capacitor side and from the OUT end of the storage branch 24 located on the side opposite the base node NB;

a storage branch 24 comprising a storage element, and preferably only the latter, said storage element comprising a capacitor C2 or a chemical storage element (and preferably only one of them); and a charge return branch 22 comprising a diode D3' (preferably only one), or several diodes mounted in the same direction (preferably in series), to the OUT end of the storage branch 24 located on the side opposite the base node NB and from the biasing node (P) located in the generating branch 21 between the variable capacitor Cv and the biasing capacitor C1.

This circuit is a direct transposition of the basic circuit in FIG. 4, obtained by inverting all the diodes. Its operation and its characteristics are identical to the previous circuit, but the polarities of all the voltages are reversed, which may offer certain advantages depending on the technological context, for example the architecture and the other components of the device in which it is integrated.

Basic Circuit with "Mid-Point" Storage

FIG. 8 shows the power supply circuit of a device according to the invention, in a third embodiment based on the basic circuit and in which the storage capacitor is of a mid-point type connected to the rectifier.

The power supply circuit of this device comprises an electrical energy storage component (preferably formed by two capacitors connected in series) having a point that is intermediate in voltage, forming for example a mid-point, which is connected to the base node NB and thus delimits:

a first storage part C2 which forms the storage element of the storage branch 24; and a second storage part C3 which is connected in series in the rectifier circuit 23 between the base node NB and the biasing node S located in the generating branch 21 between the variable capacitor Cv and the biasing capacitor C1.

In this configuration, the voltage Vmax is equal to 3/2*Vout and the voltage Vmin is equal to ½*Vout.

The energy converted per cycle is therefore expressed as follows:

$$W\text{max} = \frac{Vout^2}{2} \cdot C\text{min}\left(\frac{C\text{max}}{C\text{min}} - 3\right) \tag{5}$$

The energy generated per cycle is therefore lower than that of the basic circuit in FIG. 4, but this architecture may offer other advantages, for example the availability of several voltages at the output of the storage device or spatial distribution of the different storage parts.

Basic Circuit with Switch

FIG. 9 shows the power supply circuit of a device according to the invention, in a fourth embodiment comprising the basic circuit in FIG. 4 additionally provided with a switch.

In the power supply circuit of this device, the rectifier circuit 24 comprises, in a branch forming a single direction between the base node NB and the output node S of the end of the generating branch 21 located on the biasing capacitor C1 side, a component K forming a switch, which is arranged so as to be able to open said branch at the request of a user or in a controlled manner according to a period of time comprising a plurality of cycles of the variable capacitor Cv, and for example more than 100 or even 1000 cycles, but not necessarily a whole number of cycles.

Thus, the power supply circuit has a "passive time" (as defined above) that corresponds to the period of actuation of this switch. This switch is for example controlled by a timing circuit independent of the operation of the variable capacitor, for example a simple RC circuit. In this case, the operation of the power supply circuit may also be regarded as self-synchronizing even for a duration covering the actuation of the switch, and for example permanently.

This circuit is derived from the basic circuit in FIG. 4, by adding a switch K mounted in series with the diode D2. When the switch K is open, the device does not generate energy but it pre-charges the biasing element C1 to a voltage that tends towards:

$$Vout \cdot \left(\frac{Cmax}{Cmin} - 1\right)$$

When the switch is closed, the device generates energy in the same way as the basic circuit.

Opening the switch K periodically allows the various imperfections of the circuit to be compensated, so as to maintain a biasing voltage that is as high as possible. This can be programmed for example every minute or every hour, automatically or manually or when there is a particular movement or absence of movement, for example in the case of a cardiac pacemaker.

In the configuration where the switch K is closed and where the biasing element C1 is charged to its maximum, i.e. with a voltage equal to $$Vout \cdot \left(\frac{Cmax}{Cmin} - 1\right),$$

the voltage Vmax is equal to Vout*Cmax/Cmin and the voltage Vmin is equal to $$Vout \cdot \left(\frac{Cmax}{Cmin} - 1\right).$$

The energy converted per cycle is therefore expressed as follows:

$$Wmax = Vout^2 \cdot Cmax\left(\frac{Cmax}{Cmin} - 2\right) \qquad (6)$$

On the curves shown in FIG. 15, it can be seen that this circuit produces more energy per cycle than the circuit in FIG. 1 when the value of the ratio Cmax/Cmin is between 1 and 5.

Embodiments with a Voltage Multiplier

The invention additionally proposes integrating a circuit of the voltage multiplier type within the electric power supply circuit of the device. This characteristic of using a voltage multiplier is proposed here with the architecture of the basic circuit in FIG. 4. The invention also envisages using it in combination with the different variants described for this basic circuit, in particular with the second, third and fourth embodiments.

Figure 10A:
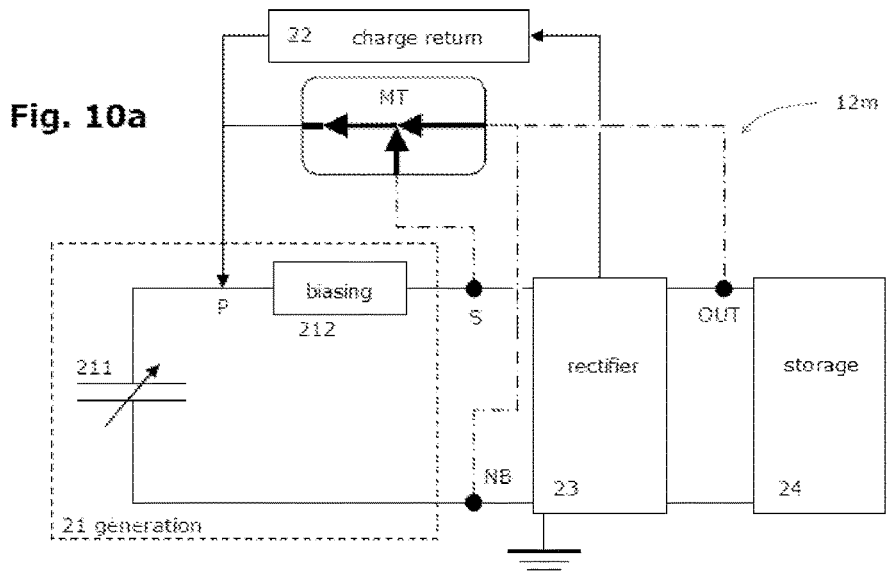
FIG. 10a is a diagram illustrating the power supply circuit of a device according to the invention, in an embodiment example comprising a voltage multiplier.

FIG. 10a shows the power supply circuit of a device according to the invention, in a particular example of a preferred embodiment of the invention. This embodiment example itself comprises a whole family of circuits comprising a voltage multiplier, which may be constituted and connected in various ways.

In this family with a multiplier, the electric power supply circuit 12m comprises a circuit MT arranged to form a voltage multiplier circuit, which is connected to the generating branch 21 via the biasing node P located between the variable capacitor 211 and the biasing capacitor 212. This multiplier MT is arranged and connected for applying, at this biasing node P, a voltage that is multiplied relative to the voltage that exists between on the one hand the output node S of the generating branch 21, and on the other hand: either the base node NB or one of the ends of the storage branch 24, for example the OUT end located between the storage branch 24 and the rectifier 23 on the biasing capacitor 212 side.

This family with multipliers may be used with the different types of multiplier circuits MT, in particular those with three ports, and in numerous configurations, some of which are detailed hereunder. These various multipliers and their connections are applicable to numerous variants of the power supply circuit described in FIG. 3, in particular but non-limitatively the "basic" circuit in FIG. 4 as well as those of the embodiments described in FIG. 7, FIG. 8 and FIG. 9.

With certain types of multipliers and according to certain connections, the role of the charge return branch 22 is fulfilled by the multiplier MT and does not comprise components or conductors of its own, as for example in FIG. 10b described below.

Figure 10B:
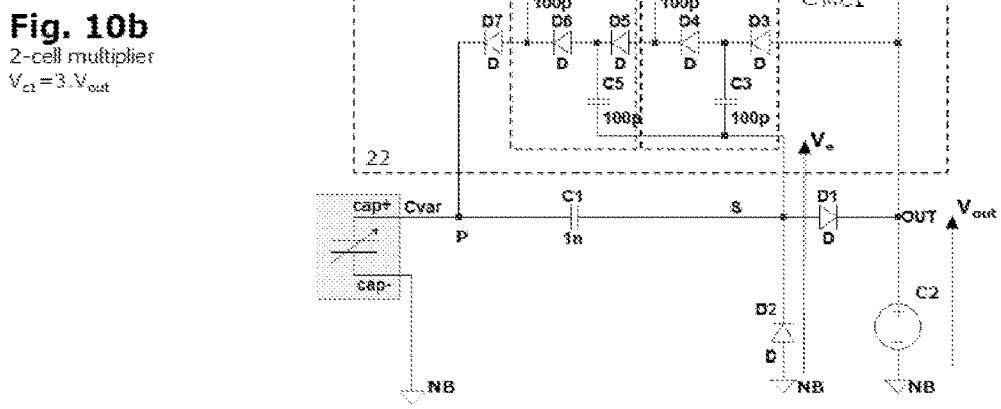
FIG. 10b illustrates the embodiment with voltage multiplier in FIG. 10a, in a particular example with two cells.

Thus, FIG. 10b illustrates an embodiment example based on the circuit in FIG. 4 called the "basic circuit" here, with a simple multiplier of the type called parallel type with two cells in cascade. In this example, the charging circuit 22 of the biasing element C1 is a voltage multiplier based on diodes (preferably diodes D that are all identical to one another and to the other diodes of the power supply circuit) and capacitors. The voltage Vout is a DC voltage. The voltage Ve is a voltage that varies periodically between 0 and Vout. Each cell adds a voltage Vout. Thus, at the biasing node P, the biasing voltage Vc1 is equal to (n+1)*Vout, where 'n' is the number of cells. The number of cells may be selected as required. The voltage Vmax is equal to (n+1)*Vout and the voltage Vmin is equal to n*Vout.

This example illustrates the case of a voltage multiplier with two cells MC1 and MC2 (n=2), which gives a biasing voltage $V_{c1}=3 \cdot V_{OUT}$. Accordingly, the energy converted per cycle is expressed as follows:

$$W = n \cdot Vout^2 \cdot Cmin\left(\frac{Cmax}{Cmin} - \frac{n+1}{n}\right) \qquad (7)$$

Evaluation of Performance

FIG. 15 shows the theoretical energy performance per cycle, obtained by simulation for different embodiments of the electric power supply circuit of a device according to the invention.

It can be seen that the embodiments with multipliers can improve the theoretical performance relative to the basic circuit, but it should be noted that this is at the price of greater complexity, which may make it bulky, and may cause larger parasitic losses. These solutions may be preferred for example if more space is available, or for example if the variable capacitor has a low Cmax/Cmin ratio (for example less than 2). The basic versions or those with few cells may be preferred for example for greater miniaturization, or if the variable capacitor has a large Cmax/Cmin ratio (for example greater than 2).

Different Types of Multipliers

More generally, the invention proposes a whole family of power supply circuits, distributed in four embodiments each covering a type of connection of the voltage multiplier. Each of these embodiments of the invention may be implemented with multipliers with more or fewer cells, producing different multiplication factors.

Thus, FIG. 11 to FIG. 14 illustrate these four embodiments of the invention, in which the power supply circuit comprises a circuit arranged to form a voltage multiplier circuit that is connected to the generating branch between the variable capacitor and the biasing capacitor, for applying a voltage there that is multiplied relative to the voltage that exists between:

on the one hand the output node S of the generating branch 21, and on the other hand the base node or one of the ends of the storage branch.

This voltage multiplier may be of various types, for example of known types. In particular, it is envisaged that the voltage multiplier circuit is a cascade multiplier of a series type or a cascade multiplier of a parallel type.

Multiplier Integrated According to the Type 1 Architecture

Figure 11:
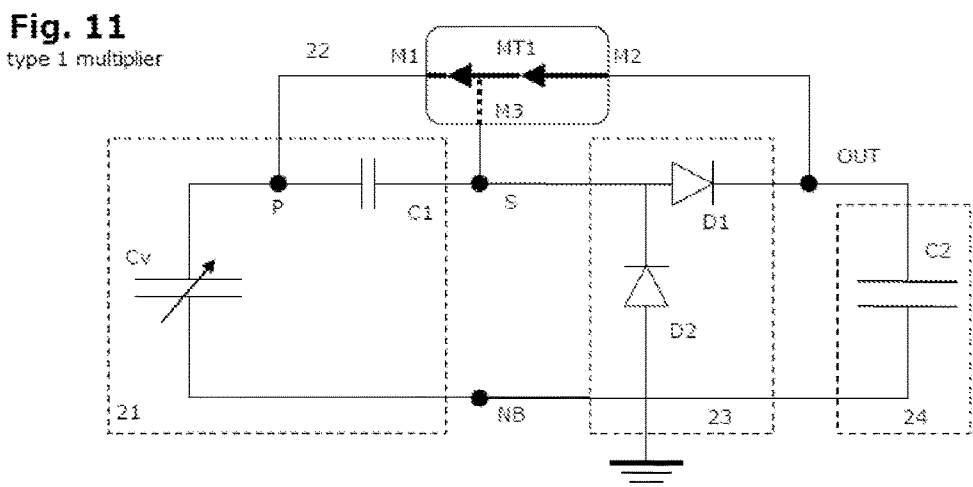
FIG. 11 is a schematic diagram illustrating the power supply circuit of a device according to the invention, in a fifth embodiment based on the basic circuit in a family of versions according to a variant called type 1 comprising a voltage multiplier circuit integrated in the charge return branch from the storage device to the variable capacitor.

FIG. 11 shows the power supply circuit of a device according to the invention, in a fifth embodiment based on the basic circuit in FIG. 4, in a version according to a variant called type 1. In this embodiment, the power supply circuit comprises a voltage multiplier circuit MT1 integrated in the charge return branch 22 from the storage device 24 to the biasing node P located in the generating branch 21 between the variable capacitor Cv and the biasing capacitor C1.

In this embodiment, the multiplier circuit comprises a cascade multiplier that contributes to the function of the charge return circuit, for example mounted in series with, or within, the charge return circuit 22. This multiplier circuit MT1 comprises at least one first branching node M1, a second branching node M2 and a third branching node M3. In the same way as in the example in FIG. 10b, it is mounted according to a first configuration so that:

a first branching node M1 and a second branching node M2 between them form a branch able to conduct a unidirectional current (i.e. always in the same direction, even if it is interrupted in time), represented by the arrow shown in bold. These two nodes are connected for the one, M2, to the biasing node P located in the generating branch 21 between the variable capacitor Cv and the biasing capacitor C1, and for the other, M1, to the OUT end of the storage branch 24 of the side opposite the base node NB;

a third node is connected to the output node S.

Multiplier Integrated According to the Type 2 Architecture

Figure 12:
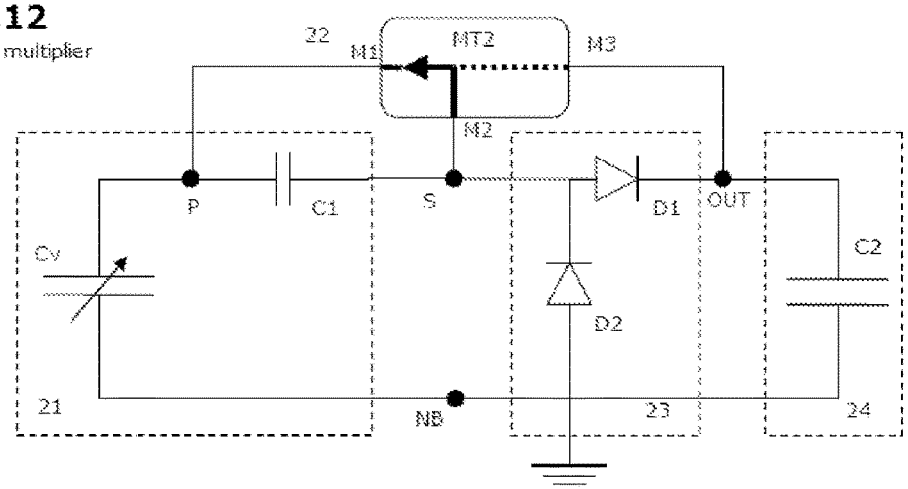
FIG. 12 is a schematic diagram illustrating the power supply circuit of a device according to the invention, in a sixth embodiment based on the basic circuit in a family of versions according to a variant called type 2 comprising a voltage multiplier circuit integrated in the charge return branch from the output node to the variable capacitor.

FIG. 12 shows the power supply circuit of a device according to the invention, in a sixth embodiment based on the basic circuit in FIG. 4, in a version according to a variant called type 2. In this embodiment, the power supply circuit comprises a voltage multiplier circuit MT2 integrated in the charge return branch 22 from the output node S to the variable capacitor Cv.

In this embodiment, the multiplier circuit MT2 comprises a cascade multiplier that contributes to the charge return circuit and that comprises at least a first, a second and a third branching node M1, M2, M3 and is mounted according to a second configuration so that:

the first branching node M1 and the second branching node M2 between them form a branch able to conduct a unidirectional current, for example a direct current, represented by the arrow shown in bold. These two nodes are connected for the one, M1, to the biasing node P located in the generating branch 21 between the variable capacitor Cv and the biasing capacitor C1, and for the other, M2, to the output node S;

the third branching node M3 is connected to the OUT end of the storage branch 24 on the side opposite the base node NB.

Multiplier Integrated According to the Type 3 Architecture

Figure 13:
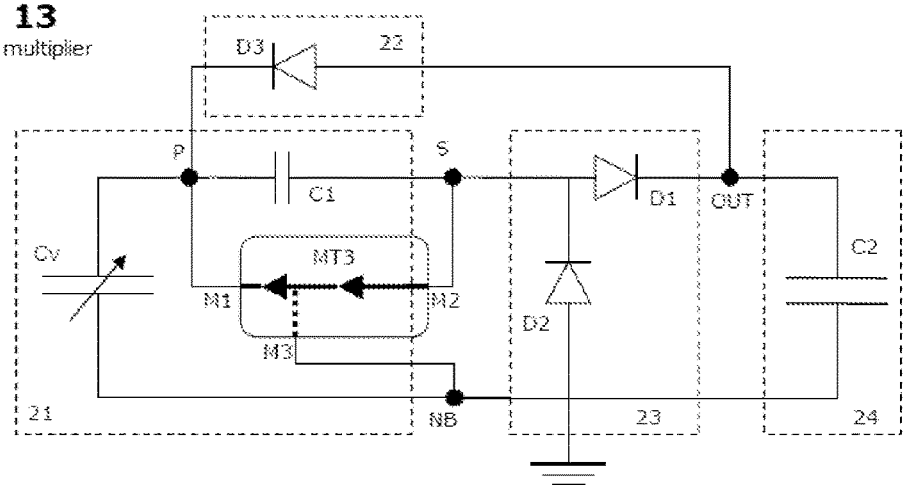
FIG. 13 is a schematic diagram illustrating the power supply circuit of a device according to the invention, in a seventh embodiment based on the basic circuit in a family of versions according to a variant called type 3 comprising a voltage multiplier circuit integrated in the generating branch from the output node to the variable capacitor.

FIG. 13 shows the power supply circuit of a device according to the invention, in a seventh embodiment based on the basic circuit in FIG. 4, in a version according to a variant called type 3. In this embodiment, the power supply circuit comprises a voltage multiplier circuit MT3 integrated in the generating branch 21 from the output node S to the variable capacitor Cv.

In this embodiment, the multiplier circuit MT3 is a cascade multiplier that comprises at least a first, a second and a third branching node M1, M2, M3 and is mounted according to a third configuration so that:

the first branching node M1 and the second branching node M2 between them form a branch able to conduct a unidirectional current, represented by the arrow shown in bold. These two nodes are connected for the one, M1, to the biasing node P located in the generating branch 21 between the variable capacitor Cv and the biasing capacitor C1, and for the other, M2, to the output node S;

the third branching node M3 is connected to the base node NB.

Multiplier Integrated According to the Type 4 Architecture

Figure 14:
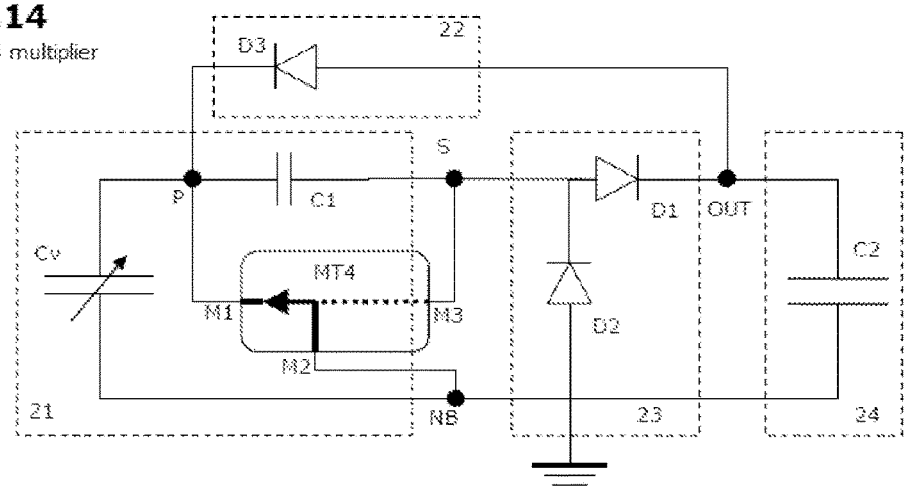
FIG. 14 is a schematic diagram illustrating the power supply circuit of a device according to the invention, in an eighth embodiment based on the basic circuit in a family of versions according to a variant called type 4 comprising a voltage multiplier circuit integrated in the generating branch from the base node to the variable capacitor.

FIG. 14 shows the power supply circuit of a device according to the invention, in an eighth embodiment based on the basic circuit in FIG. 4, in a version according to a variant called type 4. In this embodiment, the power supply circuit comprises a voltage multiplier circuit MT4 integrated in the generating branch 21 from the base node NB to the variable capacitor CV.

In this embodiment, the multiplier circuit MT4 is a cascade multiplier that comprises at least a first, a second and a third branching node M1, M2, M3 and is mounted according to a fourth configuration so that:

the first branching node M1 and the second branching node M2 between them form a branch able to conduct a unidirectional current, represented by the arrow shown in bold. These two nodes are connected for the one M1 to the biasing node P located in the generating branch 21 between the variable capacitor Cv and the biasing capacitor C1, and for the other M2 to the base node NB;

the third branching node M3 is connected to the output node S.

Examples of Circuits with Multipliers

FIG. 16 to FIG. 32 show particular examples of power supply circuit proposed for a device according to the invention, in one of the embodiments with a multiplier of types 1 to 4, with a storage element V3, which may also be an electrochemical accumulator.

Figure 16:
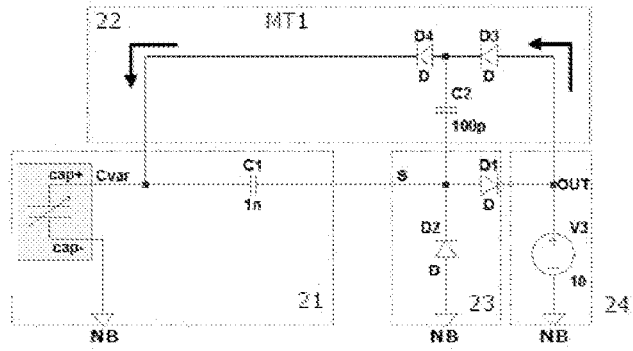
Figure 17:
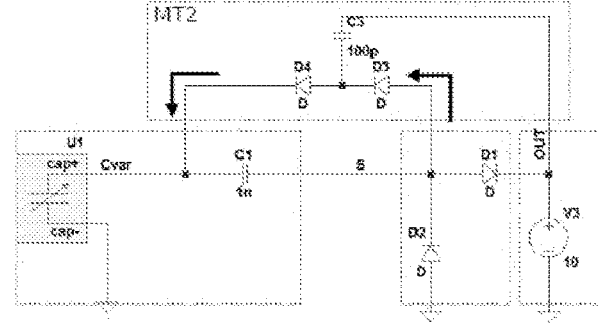
in FIG. 17, a voltage multiplier of type 2 of the parallel type, with a factor of 1.

FIG. 16 to FIG. 17: with a voltage multiplier with a factor of 1, i.e. with Vc1=Vout. This type of multiplier is proposed in a version of type 1 in FIG. 16 and of type 2 in FIG. 17. It may be regarded as a parallel type or a series type.

Figure 18:
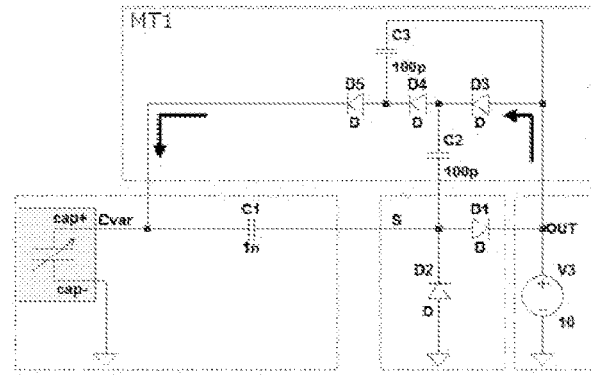
in FIG. 18, a voltage multiplier of type 1 of the parallel type, with a factor of 2.
Figure 19:
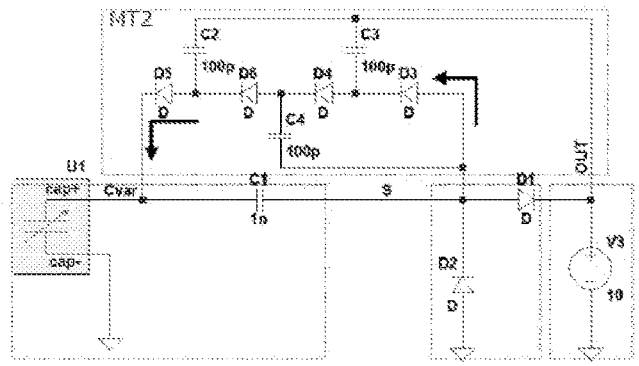
in FIG. 19, a voltage multiplier of type 2 of the parallel type, with a factor of 2.
Figure 20:
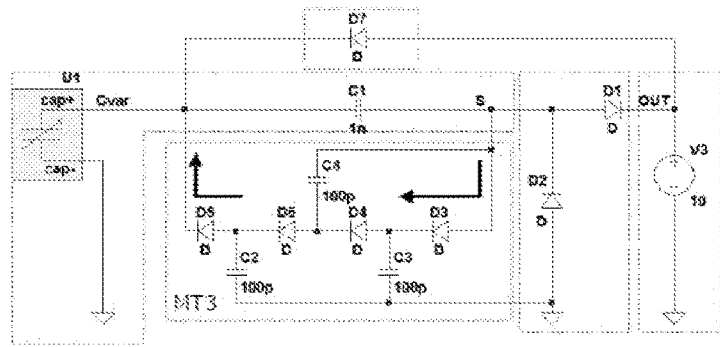
in FIG. 20, a voltage multiplier of type 3 of the parallel type, with a factor of 2.
Figure 21:
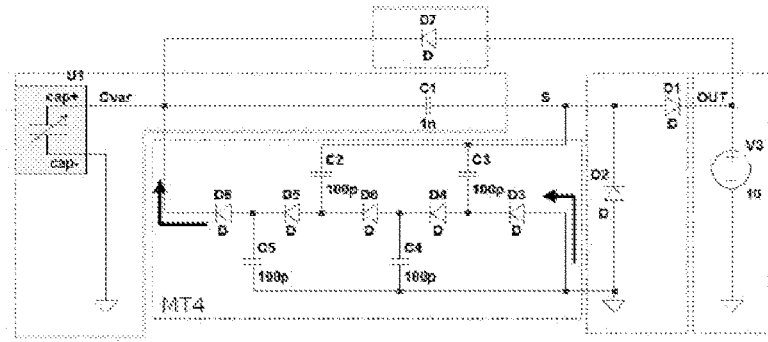
in FIG. 21, a voltage multiplier of type 4 of the parallel type, with a factor of 2.
Figure 22:
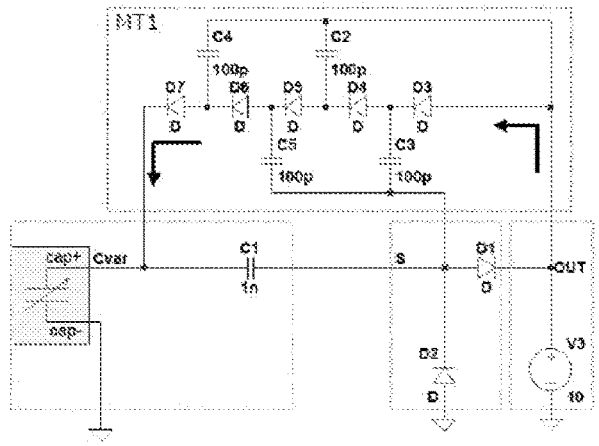
in FIG. 22, a voltage multiplier of type 1 of the parallel type, with a factor of 3, identical to that in FIG. 10b.
Figure 23:
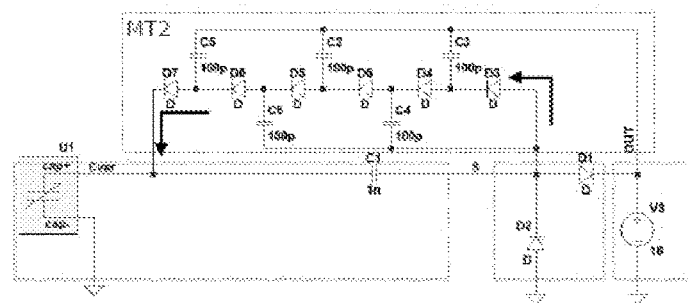
in FIG. 23, a voltage multiplier of type 2 of the parallel type, with a factor of 3.

FIG. 18 to FIG. 21: with a voltage multiplier of parallel type with a factor of 2, i.e. with Vc1=2.Vout. This type of multiplier is proposed in the following versions:

in FIG. 18, of type 1,
in FIG. 19, of type 2,
in FIG. 20, of type 3,
in FIG. 21, of type 4, In FIG. 22 and FIG. 23: with a voltage multiplier of parallel type with a factor of 3, i.e. with Vc1=3.Vout. This type of multiplier is proposed in a version of type 1 in FIG. 22 (the circuit of which is identical to that in FIG. 10b), and of type 2 in FIG. 23.

Figure 24:
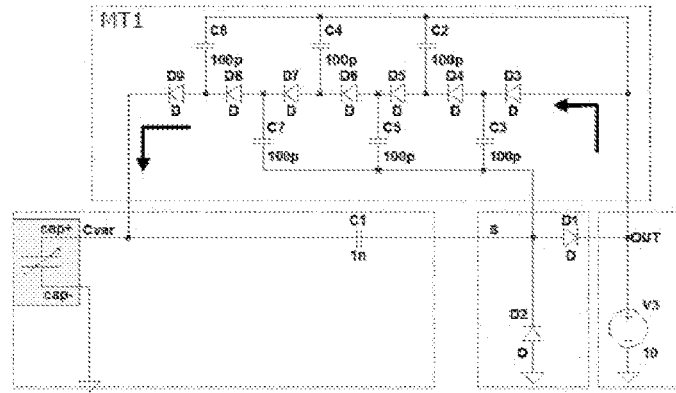
in FIG. 24, a voltage multiplier of type 1 of the parallel type, with a factor of 4.
Figure 25:
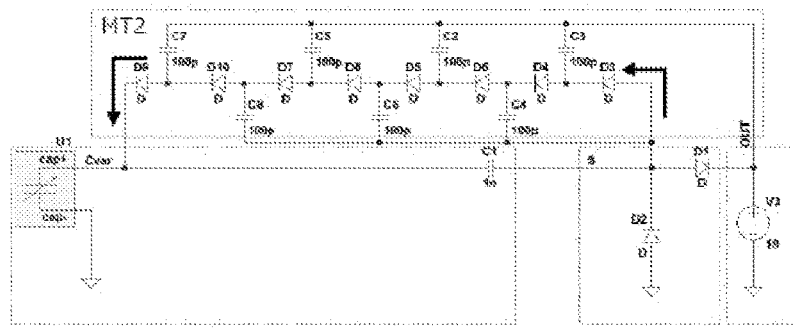
in FIG. 25, a voltage multiplier of type 2 of the parallel type, with a factor of 4.

In FIG. 24 and FIG. 25: with a voltage multiplier of parallel type with a factor of 4, i.e. with Vc1=4.Vout. This type of multiplier is proposed in a version of type 1 in FIG. 24 and of type 2 in FIG. 25.

Figure 26:
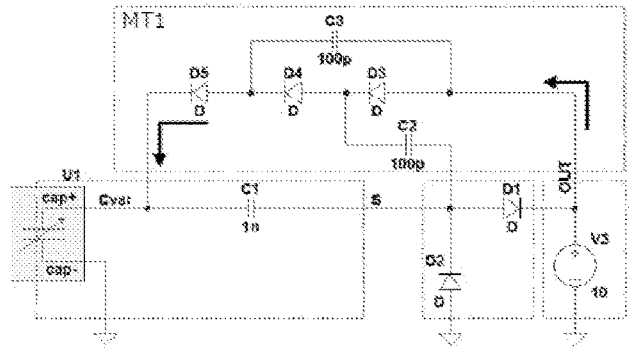
in FIG. 26, a voltage multiplier of type 1 of the series type, with a factor of 2.
Figure 27:
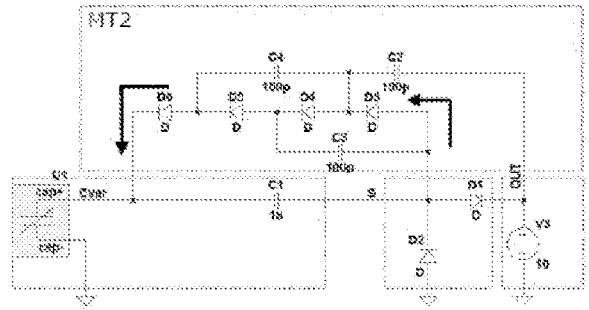
in FIG. 27, a voltage multiplier of type 2 of the series type, with a factor of 2.
Figure 28:
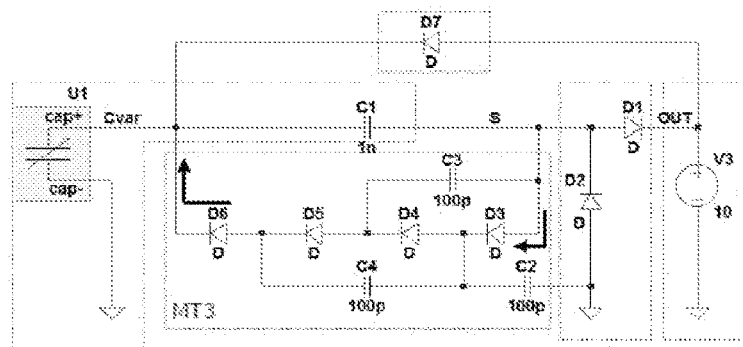
in FIG. 28, a voltage multiplier of type 3 of the series type, with a factor of 2.
Figure 29:
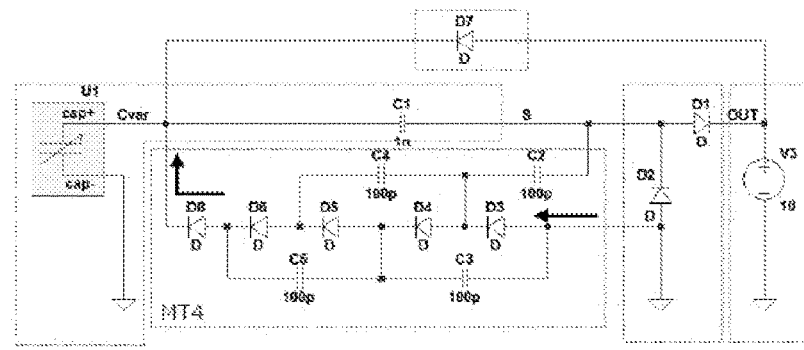
in FIG. 29, a voltage multiplier of type 4 of the series type, with a factor of 2.

In FIG. 26 to FIG. 29: with a voltage multiplier of series type with a factor of 2, i.e. with Vc1=2.Vout. This type of multiplier is proposed in the following versions:

in FIG. 26, of type 1,
in FIG. 27, of type 2,
in FIG. 28, of type 3,
in FIG. 29, of type 4.

Figure 30:
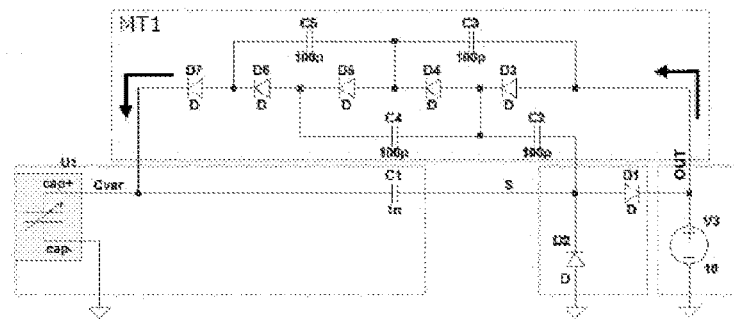
in FIG. 30, a voltage multiplier of type 1 of the series type, with a factor of 3.
Figure 31:
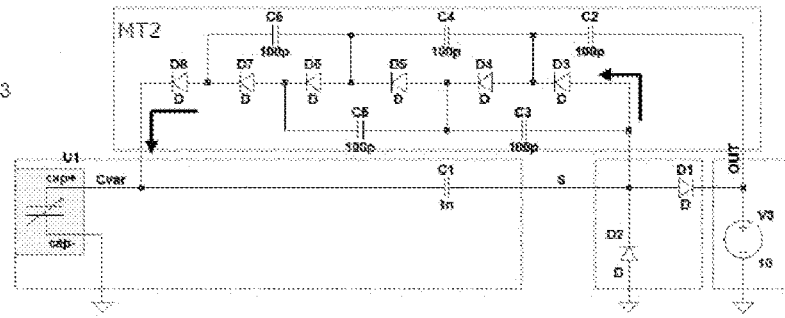
in FIG. 31, a voltage multiplier of type 2 of the series type, with a factor of 3.

In FIG. 30 and FIG. 31: with a voltage multiplier of series type with a factor of 3, i.e. with Vc1=3.Vout. This type of multiplier is proposed in a version of type 1 in FIG. 30 and of type 2 in FIG. 31.

In FIG. 24 and FIG. 25: with a voltage multiplier of parallel type with a factor of 4, i.e. with Vc1=4.Vout. This type of multiplier is proposed in a version of type 1 in FIG. 24 and of type 2 in FIG. 25.

Variants with Full-Bridge Rectifier

Figure 32:
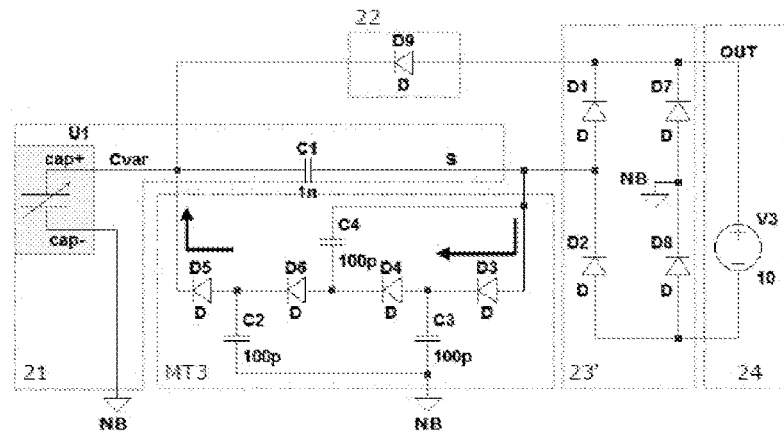
FIG. 32 and FIG. 33 are diagrams showing the power supply circuit of a device according to the invention of one of the embodiments with a multiplier, in versions with a rectifier circuit formed by a "full" bridge with 4 diodes.
Figure 33:
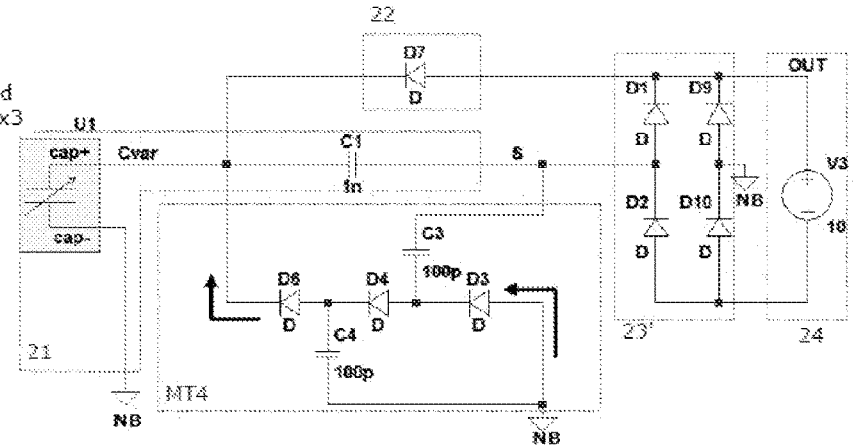

FIG. 32 and FIG. 33 show the power supply circuits of a device according to the invention of one of the embodiments with a multiplier, in versions with a rectifier circuit formed by a "full" bridge with 4 diodes, and:

in FIG. 32, a voltage multiplier of type 3 of the parallel type, with a factor of 4;
in FIG. 33, a voltage multiplier of type 4 of the series type, with a factor of 3.

In these embodiments, the rectifier circuit (23') comprises at least one bridge of at least four diodes forming:

at least two branches (D1 and D7, or D1 and D9) forming a unidirectional connection to the end (OUT) of the storage branch (24) on the side of the charge return branch (22), from the output node (S) and from the base node (NB), respectively; and at least two branches (D2 and D8, or D2 and D10) forming a unidirectional connection from the end of the storage branch (24) on the side opposite the charge return branch (22), to the output node (5) and to the base node (NB), respectively.

Examples of Applications

As an order of magnitude, such a power supply circuit makes it possible to envisage an energy efficiency of more than 80% for a storage voltage of 5V. The device according to the invention is envisaged more particularly for making, or for being incorporated in, for example:

a medical implant, such as a cardiac pacemaker or an implanted monitoring device;
a device incorporated in a portable element, such as clothing, footwear, jewelry, bracelet, headband, earphone;
a device transmitting information by environmental detection, measurement or monitoring, such as a fixed or dispersed sensor, or a data repeater or autonomous sensor on board a vehicle.

Of course, the invention is not limited to the examples that have just been described and numerous adjustments may be made to these examples while remaining within the scope of the invention. However, a particular preferred characteristic of the invention is formed by all or part of the different examples described here and combinations specified here.

The invention claimed is:

1. An electronic device of the type operating without an external power supply, comprising: an electric power supply circuit arranged for supplying said device, said electric power supply circuit being arranged for supplying energy for operation of said electronic device via a storage element;

said electric power supply circuit comprising at least one component, called a variable capacitor, having an electrical capacitance that varies under the effect of an alternating mechanical movement, said variable capacitor being arranged to receive said mechanical movement from the environment of said electronic device;

and being connected to said storage device by means of a rectifier circuit to increase the electrical energy stored there;

said device said electric power supply circuit comprises:

a generating branch formed by at least the variable capacitor and a biasing capacitor mounted in series, said generating branch being mounted in parallel with the rectifier circuit and with a storage branch comprising the storage element, between a node, called base node, that is located at the end of the generating branch on the variable capacitor side and is maintained at a reference potential;

a node, called output node, located at the end of the generating branch on the biasing capacitor side;

a charge return branch of a type able to conduct a unidirectional electric current:

to the generating branch, by at least one first end connected to a node, called a biasing node, which is located in the generating branch between the variable capacitor and the biasing capacitor;

from the rectifier, by at least one second end receiving a part of the electrical energy produced by said power supply circuit; and the assembly formed by said generating branch, the rectifier circuit, the storage branch and the charge return branch constitutes an electric circuit the behaviour of which is passive and remains unchanged and permanent in its characteristics during at least one plurality of cycles of the variable capacitor;

thus carrying out at each cycle an additional charge of the biasing capacitor C according to an operating mode that is self-synchronizing, i.e. it does not require any means for synchronization with respect to the mechanical movements during said plurality of cycles;

and in that the electric power supply circuit comprises a circuit arranged to form a voltage multiplier circuit that is connected to the generating branch at a biasing node located between the variable capacitor and the biasing capacitor, for applying a voltage there that is multiplied relative to the voltage that exists between on the one hand the output node of said generating branch, and on the other hand the base node or one of the ends of the storage branch.

2. The device according to claim 1, characterized in that the charge return branch comprises an oriented diode from the rectifier to the generating branch, or several diodes mounted in the same direction, and preferably in series.

3. The device according to claim 1, characterized in that the electric power supply circuit, or at least one or more of the circuits among the generating branch, the storage branch, the charge return branch and the rectifier circuit, is made so that it only comprises passive components and non-driven semiconductors, and in particular only diodes and capacitors.

4. The device according to claim 1, characterized in that the power supply circuit comprises the following elements, and preferably only these:
   a generating branch comprising the variable capacitor and one or more biasing capacitors, and preferably only these latter, said generating branch being connected via its base node to a reference potential, via a node that is common to the rectifier and to the storage branch;
   a rectifier circuit comprising the following components, and preferably only these:
   a diode, or several diodes mounted in the same direction, from the base node and to the end of the generating branch located on the biasing capacitor side;
   a diode, or several diodes mounted in the same direction, from the end of the generating branch located on the biasing capacitor side and to the end of the storage branch located on the side opposite the base node;
   a storage branch comprising a storage element, and preferably only the latter, said storage element comprising a capacitor or a chemical storage element; and
   a charge return branch comprising a diode, or several diodes mounted in the same direction, from the end of the storage branch located on the side opposite the base node and to a biasing node of the generating branch located between the variable capacitor and the biasing capacitor.

5. The device according to claim 1, characterized in that the power supply circuit comprises the following elements, and preferably only these:
   a generating branch comprising the variable capacitor and one or more biasing capacitors, and preferably only the latter, said generating branch being connected to earth or to a reference potential via the base node;
   a rectifier circuit comprising the following components, and preferably only these:
   a diode, or several diodes mounted in the same direction, to the base node and from the end of the generating branch located on the biasing capacitor side;
   a diode, or several diodes mounted in the same direction, to the end of the generating branch located on the biasing capacitor side and from the end of the storage branch located on the side opposite the base node;
   a storage branch comprising a storage element, and preferably only these latter, said storage element comprising a capacitor or a chemical storage element; and
   a charge return branch comprising a diode, or several diodes mounted in the same direction, to the end of the storage branch located on the side opposite the base node and from a biasing node of the generating branch located between the variable capacitor the biasing capacitor.

6. The device according to claim 1, characterized in that the power supply circuit comprises an electrical energy storage component having a point with intermediate voltage, forming for example a mid-point, which is connected to the base node and thus delimits:
   a first storage part that forms the storage element of the storage branch; and
   a second storage part that is mounted in series in the rectifier circuit between the base node and a biasing node of the generating branch located between the variable capacitor and the biasing capacitor.

7. The device according to claim 1, characterized in that the rectifier circuit comprises, in a branch forming a single direction between the base node and the end of the generating branch located on the biasing capacitor side, a component forming a switch and that is arranged so as to be able to open said branch at the request of a user or in a controlled manner according to a period of time comprising a plurality of cycles of the variable capacitor, and in particular more than 100 or even 1000 cycles.

8. The device according to claim 1, characterized in that the voltage multiplier circuit is a cascade multiplier of a series type or parallel type.

9. The device according to claim 8, characterized in that the multiplier circuit comprises a cascade multiplier that contributes to the function of charge return circuit and that comprises at least a first, a second and a third branching node and is mounted according to a first configuration so that:
   the first branching node and the second branching node between them form a branch able to conduct a unidirectional current, and are connected
   for the one, to a biasing node located in the generating branch between the variable capacitor and the biasing capacitor; and
   for the other, to the end of the storage branch on the side opposite the base node;
   the third branching node is connected to the output node.

10. The device according to claim 1, characterized in that the multiplier circuit comprises a cascade multiplier that contributes to the charge return circuit and that comprises at least a first, a second and a third branching node and is mounted according to a second configuration so that:
   the first branching node and the second branching node between them form a branch able to conduct a unidirectional current, and are connected
   for the one, to a biasing node located in the generating branch between the variable capacitor and the biasing capacitor; and
   for the other, to the output node;
   the third branching node is connected to the end of the storage branch on the side opposite the base node.

11. The device according to claim 1, characterized in that the multiplier circuit is a cascade multiplier that comprises at least a first, a second and a third branching node and is mounted according to a third configuration so that:
   the first branching node and the second branching node between them form a branch able to conduct a unidirectional current, and are connected
   for the one, to a biasing node P located in the generating branch between the variable capacitor and the biasing capacitor; and
   for the other, to the output node;
   the third branching node is connected to the base node.

12. The device according to claim 1, characterized in that the multiplier circuit is a cascade multiplier that comprises at least a first, a second and a third branching node and is mounted according to a fourth configuration so that:

the first branching node and the second branching node between them form a branch able to conduct a unidirectional current, and are connected for the one, to a biasing node located in the generating branch between the variable capacitor the biasing capacitor; and for the other, to the base node;

the third branching node is connected to the output node.

13. The device according to claim 1, characterized in that the biasing capacitor has an electrical capacitance having a value of at least five times the variation in the capacitance of the variable capacitor during a cycle, and/or in that the storage element has an electrical energy storage capacity corresponding to a capacitor the electrical capacitance of which is greater than three times that of the biasing capacitor.

14. The device according to claim 1, characterized in that the rectifier circuit comprises at least one bridge of at least four diodes forming:

at least two branches forming a unidirectional connection to the end of the storage branch on the side of the charge return branch, from the output node and from the base node, respectively; and at least two branches forming a unidirectional connection from the end of the storage branch of the side opposite the charge return branch, to the output node and to the base node, respectively.

15. An electric power supply circuit arranged specifically for an electronic device according to claim 1.

16. An electronic device intended to be implanted in vivo in the human body or in the body of an animal without maintaining physical connection with the outside, comprising a power supply circuit according to claim 15.

17. An electronic device intended to be implanted in vivo in the human body or in the body of an animal without maintaining physical connection with the outside, comprising: a device according to claim 1.

* * * * *